US010466218B2

(12) United States Patent
Swager et al.

(10) Patent No.: US 10,466,218 B2
(45) Date of Patent: Nov. 5, 2019

(54) GAS SENSORS BASED UPON METAL CARBON COMPLEXES

(71) Applicant: Massachusetts Institute of Technology, Cambridge, MA (US)

(72) Inventors: Timothy M. Swager, Newton, MA (US); Sophie Liu, Cambridge, MA (US); Graham Sazama, Chestnut Hill, MA (US); Alexander R. Petty, Allston, MA (US); Jan M. Schnorr, Boston, MA (US)

(73) Assignee: MASSACHUSETTS INSTITUTE OF TECHNOLOGY, Cambridge, MA (US)

( * ) Notice: Subject to any disclaimer, the term of this patent is extended or adjusted under 35 U.S.C. 154(b) by 961 days.

(21) Appl. No.: 14/635,995

(22) Filed: Mar. 2, 2015

(65) Prior Publication Data
US 2015/0247832 A1 Sep. 3, 2015

Related U.S. Application Data

(63) Continuation of application No. 61/946,872, filed on Mar. 2, 2014.

(51) Int. Cl.
*G01N 33/00* (2006.01)
*G01N 27/12* (2006.01)
(52) U.S. Cl.
CPC ....... *G01N 33/0047* (2013.01); *G01N 27/127* (2013.01); *Y10T 436/21* (2015.01); *Y10T 436/216* (2015.01)

(58) Field of Classification Search
CPC .............. G01N 33/0047; Y10T 436/21; Y10T 436/216
See application file for complete search history.

(56) References Cited

U.S. PATENT DOCUMENTS

| 4,886,625 | A | 12/1989 | Albarella et al. |
| 4,898,985 | A | 2/1990 | Ito et al. |
| 4,926,156 | A | 5/1990 | Dickert et al. |
| 7,318,908 | B1 | 1/2008 | Dai |
| 2004/0235184 | A1 | 11/2004 | Swager |
| 2005/0022581 | A1* | 2/2005 | Sunshine ............. G01N 29/022 73/31.05 |
| 2008/0030352 | A1* | 2/2008 | Shaw ................... G01N 27/127 340/579 |
| 2009/0085071 | A1 | 4/2009 | Brongersma et al. |

(Continued)

FOREIGN PATENT DOCUMENTS

JP A-H1-274052 11/1989

OTHER PUBLICATIONS

Notification of Transmittal of the International Search Report and the Written Opinion of the International Searching Authority, or the Declaration dated Jan. 6, 2016, issued in International Application No. PCT/USUS15/18345.

(Continued)

*Primary Examiner* — Samuel P Siefke
(74) *Attorney, Agent, or Firm* — Steptoe & Johnson LLP

(57) ABSTRACT

A sensor can include a conductive region in electrical communication with at least two electrodes, the conductive region including a conductive material and an alkene-interacting metal complex.

13 Claims, 12 Drawing Sheets

Ar = $C_6H_5$, [Co(tpp)Cl]
Ar = $C_6F_5$, [Co(tpfpp)Cl]

Ar = $C_6H_5$, [Co(tpp)]$ClO_4$
Ar = $C_6F_5$, [Co(tpfpp)]$ClO_4$

(56) References Cited

U.S. PATENT DOCUMENTS

2011/0089051 A1 4/2011 Wang et al.
2013/0273665 A1* 10/2013 Swager ................. G01N 27/12
436/142

OTHER PUBLICATIONS

International Search Report dated Jan. 6, 2016, issued in International Application No. PCT/USUS15/18345.
Written Opinion of the International Searching Authority dated Jan. 6, 2016, issued in International Application No. PCT/USUS15/18345.
PCT/US2015/018345 Notification Concerning Transmittal of International Preliminary Report on Patentability [PCT/IB/326] dated Sep. 15, 2016.
Office Action from JP 2016-555290, dated Feb. 5, 2019.

* cited by examiner

US 10,466,218 B2

GAS SENSORS BASED UPON METAL CARBON COMPLEXES

PRIORITY CLAIM

This application claims priority to U.S. application Ser. No. 61/946,872, filed Mar. 2, 2014, which is incorporated by reference in its entirety.

FEDERALLY SPONSORED RESEARCH OR DEVELOPMENT

This invention was made with government support under Contract No. W911NF-13-D-0001 awarded by the Army Research Office. The government has certain rights in the invention.

TECHNICAL FIELD

The invention relates to sensor compositions based on metal complexes.

BACKGROUND

Ethylene gas is an analyte of considerable importance to industries related to produce and agriculture. Due to its small size and limited chemical functionality, however, ethylene is a challenging chemical analyte to detect. Currently available methods for determining the concentration of ethylene suffer from high cost and impracticality of implementation in the field.

SUMMARY

In general, a chemiresponsive composition can include a metal complex including a metal that binds to and activates an alkene such that it reacts with a nucleophile to provide a metal complex with a metal carbon single bond. The chemiresponsive composition changes properties, for example, conductivity properties, upon exposure to a compound of interest. The metal complex can react with the alkene to produce a chemiresistive response in the composition. The metal complex can further react to regenerate the metal complex that reacts with an additional alkene.

In one aspect, a sensor can include a conductive region in electrical communication with at least two electrodes, the conductive region including a conductive material and an alkene-interacting metal complex.

In another aspect, a method of sensing an analyte can include exposing a sensor to a sample, the sensor including a conductive region in electrical communication with at least two electrodes, the conductive region including a conductive material and an alkene-interacting metal complex, and measuring an electrical property at the electrodes. The electrical property can be resistance or conductance, for example, of the conductive region.

In certain embodiments, the sample can be a gas.

In certain embodiments, the analyte can be ethylene, 1-methylcyclopropene, butadiene, isoprene, carbon monoxide or acetylene.

In certain embodiments, the conductive material can include a carbon nanotube, graphite, graphene, the alkene-interacting metal complex, a conductive polymer, a metal oxide, or an inorganic semiconductor.

In certain embodiments, the alkene-interacting metal complex can include a metal macrocycle complex capable of forming a stable complex by reaction with an alkene. The macrocycle complex can include a phthalocyanine or a porphyrin. The macrocycle complex includes Mn, Re, Fe, Ru, Os, Co, Rh, Ir, Ni, Pd, Pd, Cu, Ag, Au, or Hg, for example, a cobalt ion, iridium ion, or palladium ion. For example, the metal macrocycle complex can include a 5, 10, 15, 20-tetraphenylporphyrinato cobalt or a 5, 10, 15, 20-tetrakis(pentafluorophenyl)porphyrinato cobalt.

In certain embodiments, the metal macrocycle complex can include a non-coordinating anion, for example, Cl—, ClO4-, BF4-, RSO3- where R is $CF_3$, $CH_3$, an aryl, an alkyl, or an oxygen bound alkyl or aryl group, PF6-, or BAr4-, where Ar is an aromatic group (for example, the alkyl or aryl groups can be C1-C8 alkyl or C6-C14 aryl or heteroaryl groups). For example, the alkene-interacting metal complex can include palladium(II) trifluoroacetate or palladium(II) acetate.

In another aspect, a method of preparing a sensor can include forming a complex including a conductive region in electrical communication with at least two electrodes, the conductive region including a conductive material and an alkene-interacting metal complex, and placing the conductive material in electrical communication with at least two electrodes. In certain embodiments, the sensor can be read wirelessly. In other embodiments, the sensor can include a RFID tag that can be read wirelessly.

Other aspects, embodiments, and features will be apparent from the following description, the drawings, and the claims.

DETAILED DESCRPTION

Figure 1:
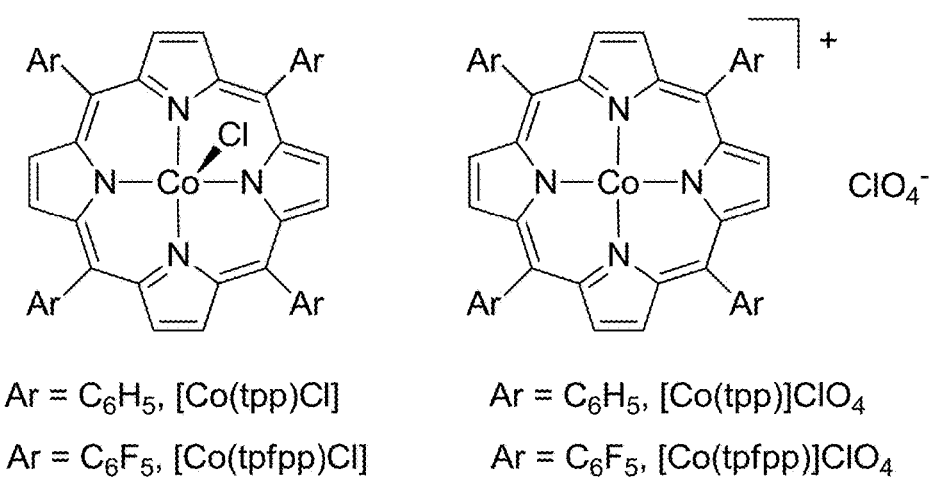
FIG. 1 shows chemical structures of cobalt(III) porphyrins employed in ethylene detectors. Aquo ligands have been omitted for clarity.

As the hormone responsible for initiating the ripening of fruit as well as other processes in plant development, ethylene gas is an analyte of considerable importance to industries related to produce and agriculture. Due to its small size and limited chemical functionality, ethylene is a challenging chemical analyte to detect. Currently available methods for determining the concentration of ethylene suffer from high cost and impracticality of implementation in the field. See, for example, Esser, B.; Swager, T. M., Angew. Chem. Int. Ed. 2010, 49, 8872-8875, which is incorporated by reference in its entirety. To address these drawbacks, a reversible chemoresistive ethylene sensor, fabricated from a sensing material comprised of single-walled carbon nanotubes (SWNTs) and hydrotris[3,5-bis(trifluoromethyl)pyrazol-1-yl]boratocopper(I), can be used. See, for example, Esser, B.; Schnorr, J. M.; Swager, T. M., Angew. Chem. Int. Ed. 2012, 51, 5752-5756, which is incorporated by reference in its entirety. However, the sensor's lifetimes are limited due to susceptibility of the copper(I) complex to aerobic oxidation and to moisture.

A sensor can include a conductive region in electrical communication with at least two electrodes, the conductive region including a conductive material and an alkene-interacting metal complex. The alkene-interacting metal complex can bind with or otherwise activate the alkene for further reaction. The alkene-interacting metal complex can include a metal macrocycle complex capable of forming a stable complex by reaction with ethylene. A macrocycle can be a cyclic macromolecule or a macromolecular cyclic portion of a molecule; it can contain a ring of nine or more atoms. The metal of the metal complex is electrophilic, for example, in a +2 or higher oxidation state. The metal complex can be in a state that has a high degree of ionic character, for example, with a positive charge on the metal center. The alkene-interacting metal complex can include a number of transition metals including Mn, Re, Fe, Ru, Os, Co, Rh, Ir, Ni, Pd, Pd, Cu, Ag, Au, or Hg. In alternative embodiments, the metal can be an actinide or lanthanide. The ligand of the metal complex can be an alpha-diimine ligand, porphyrin, or other macrocyclic ligand. Examples of alkene-interacting metal complexes include cobalt (III) or palladium(II) complexes with chloride, acetates, or trifluoroacetate ligands. These are examples of compounds that react with alkenes such as ethylene in a Wacker reaction, wherein ethylene is activated by binding to the metal and reacting with a nucleophile. Similar reactions can occur by activation with other metals, provided they bind the alkene and are sufficiently electrophilic to activate the alkene to attack by a nucleophile.

The gap between electrodes can range from 0.005 mm to 10 mm. The layer thickness of the conductive material and the alkene-interacting metal complex can be between 0.01 µm to 5 µm. The mass ratio between the alkene-interacting metal complex to the conductive material can be between 1:0.5 and 1:100. In some cases, the alkene-interacting complex can be intrinsically conductive, and no additional conductive material need be added to create a chemiresistive sensor.

The resistivity or conductivity of the sensor can change when the sensor is exposed to an analyte. A conductive material conducts electricity. The conductive material can include a carbon nanotube, a conductive polymer, an inorganic semiconductor, or a metal oxide. The conductive material can include a metal, an organic material, a dielectric material, a semiconductor material, a polymeric material, a biological material, a nanowire, a semiconducting nanoparticle, a nanofiber, a carbon fiber, a carbon particle, carbon nanotubes, graphite, graphene, carbon paste, metal particles, or conducting ink, or combination thereof. The conductive material can include an organic electronic material, a conductive polymer, a doped conjugated polymer, or a conductive inorganic material.

A conductive polymer can include a poly(fluorene), a polyphenylene, a polypyrene, a polyazulene, a polynaphthalene, a poly(pyrrole) (PPY), a polycarbazole, a polyindole, a polyazepine, a polyaniline (PANI), a poly(thiophene) (PT), a poly(3,4-ethylenedioxythiophene) (PEDOT), a poly(p-phenylene sulfide) (PPS), a poly(acetylene) (PAC), a poly (p-phenylene vinylene) (PPV), or copolymers thereof. A metal oxide can include $ZnO_2$, $SnO_2$, $TiO_4$, $WO_3$, $MoO_3$, NiO, SnO, or cobinations thereof. The inorganic semiconductor can include $MoS_2$, $MoSe_2$, $ZnS_2$, Si, Ge, InP, or combinations thereof.

An ethylene dosimeter can use the chemoresistive SWNT-based device platform with cobalt(III) porphyrins that can demonstrate increased robustness to oxygen and to water. Alkene adducts with cobalt(III) porphyrins can be reactive intermediates for the formation of organocobalt porphyrin complexes, and adducts can be formed with other π ligands (e.g., CO, $C_2H_2$). Sugimoto, H.; Ueda, N.; Mori, M., Bull. Chem. Soc. Jpn 1981, 54, 3425-3432; Setsune, J. Ito, S.; Takeda, I.; Ishimaru, Y.; Kitao, T.; Sato, M.; Ohya-Nishiguchi, H.; Organomet. 1997, 16, 597-605; Schmidt, E.; Zhang, H.; Chang, C. K.; Babcock, G. T.; Oertling, W. A., J. Am. Chem. Soc. 1996, 118, 2954-2961, each of which is incorporated by reference in its entirety.

Cobalt(III) porphyrins incorporated in a SWNT network can be active in the chemoresistive detection of ethylene. A series of cobalt(III) porphyrins can be used (FIG. 1). Sensitivity to ethylene can benefit from increasing the electrophilicity of the cobalt(III) center toward alkenes through the use of both a relatively electron-withdrawing porphyrin ligand and a weakly coordinating counter anion. Therefore, the series of cobalt(III) porphyrins can allow for comparison between 5,10,15,20-tetraphenylporphyrinato (tpp) and the more electron-withdrawing 5,10,15,20 tetrakis(pentafluorophenyl)porphyrinato (tpfpp) ligand as well as between Cl$^-$ and the more weakly coordinating $ClO_4^-$ counteranion.

Figure 2:
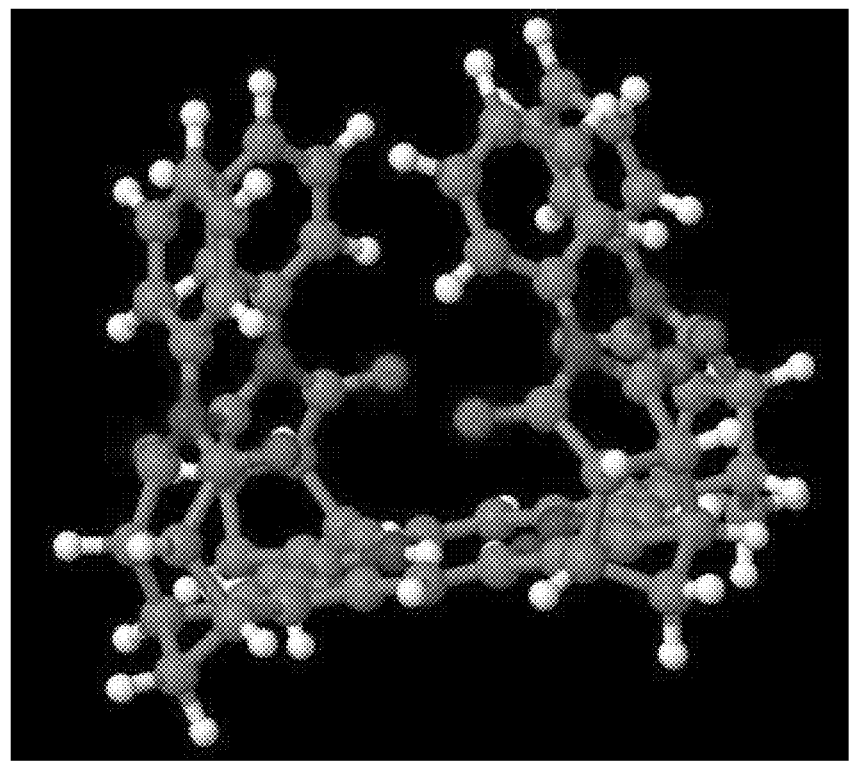
FIG. 2 shows structure of canopied pyrrole-derived porphyrin with sterically restricted metal coordination site.

Porphyrins with a sterically protected metal center may provide enhanced selectivity to ethylene by excluding compounds that are larger or that would bind to the metal center in an $\eta^1$ fashion perpendicular to the approximate plane of the porphyrin ring (e.g., CO, MeCN). A canopied pyrrole can give such protection by restricting the space around a tervalent group 9 metal center when incorporated into a porphyrin ligand's structure (FIG. 2), preventing the binding of larger interferent molecules such as bulkier alkenes and other coordinating volatile organic compounds while still allowing the particularly small molecule ethylene to access the metal center in a flatter, side-on fashion and potentially excluding larger molecules that could be forced to bind end-on due to the canopy's obstruction of space higher above the metal center. See, for example, Lee, D.; Swager, T. M., J. Am. Chem. Soc. 2003, 125, 6870-6871; Lee, D.; Swager, T. M., Chem. Mater. 2005, 17, 4622-4629, which is incorporated by reference in its entirety. Restricting the access of interferents to the metal binding site can result in increased selectivity to ethylene and increased stability to other compounds and environmental interferents when used in this gas detection platform. For example, ethylene may be detected in the presence of 1-methylcyclopropene.

A sensor including a macrocyclic metal complex, such as Co(tpp)Cl, [Co(tpp)]ClO$_4$, [Co(tpfpp)Cl], or [Co(tpfpp)] ClO$_4$, can demonstrate dosimetric response to ethylene, which can suggest that ethylene is reacting irreversibly with the cobalt(III) porphyrin complex and a nucleophile to an extent that can still be transduced chemiresistively.

A method of sensing an analyte can include exposing a sensor to a sample and measuring an electrical property at the electrodes. The sensor can include a conductive region in electrical communication with at least two electrodes, the conductive region including a conductive material and an alkene-interacting metal complex. The sample can be a gas sample. The gas sample can include ethylene. The gas sample can include hexene. The gas sample can include 1-methylcyclopropene.

A method of preparing a sensor can include forming a complex including a conductive region in electrical communication with at least two electrodes, the conductive region including a conductive material and an alkene-interacting metal complex, and placing the conductive material in electrical communication with at least two electrodes.

Organocobalt Complex Formation Mechanism

The reaction of [Co(tpp)]ClO$_4$ with ethylene in methanol-d$_4$ by $^1$H NMR at room temperature can show very weak resonances at −2.64 (t, J=8 Hz) and −4.31 ppm (t, J=8 Hz). These signals would be consistent with the formation of [Co]—CH$_2$CH$_2$OR (in the NMR experiment, R=CD$_3$); the high field chemical shifts are commensurate with spectral data of analogous products for other alkene reactions with [Co(tpp)]ClO$_4$ and are expected with the effect of the porphyrin's diamagnetic ring current at the ring's center. Furthermore, their J values are typical of vicinal H—H coupling in alkanes. The transduction of the irreversible formation of this organocobalt complex in the CNT network is consistent with the dosimetric behavior of the ethylene detector. The conductive properties of carbon nanotubes can be highly sensitive to their electronic environment, and the change in electronics and more neutral nature of the [Co] metal complex after alkylation as described in Scheme 1 are likely sufficient for chemiresistive transduction in the CNTs through a decrease in conductance.

The following Scheme 1 shows a proposed mechanism for reaction of C$_2$H$_4$ with [M] in the presence of a ROH nucleophile, where R is a carbon fragment (for example, substitued or unsubstituted alkyl or aryl) or hydrogen.

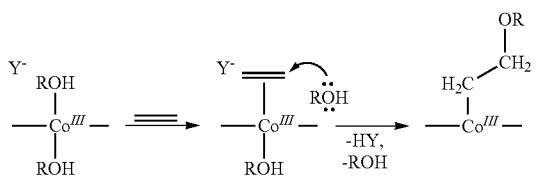

The reaction to form the presumed organocobalt complex can be proceeding by a generalized mechanism shown in Scheme 1 analogous to that previously proposed by Sugimoto and coworkers for the formation of the 2,2-diethoxyethylcobalt(III) porphyrin complex from [Co(tpp)]ClO$_4$ and ethyl vinyl ether in the presence of ethanol. See, for example, Sugimoto, H.; Nagano, M.; Yoshida, Z.; Ogoshi, J., *Chem. Lett.* 1980, 521-524, which is incorporated by reference in its entirety. The ethylene displaces a ligand, then becomes hydrated and deprotonated, all without a formal oxidation state change at the metal center.

These steps can also occur in the Wacker process for the oxidation of alkenes using catalytic Pd$^{2+}$ (Scheme 2), which can also be employed for ethylene sensing as PdCl$_2$ or as supported by ligands other than chloride such as α-diimine. See, for example, Winston, M. S.; Obland, P. F.; Labinger, J. A.; Bercaw, J. E., *Angew. Chem. Int. Ed.* 2012, 51, 9822-9824, which is incorporated by reference in its entirety. Several different incarnations of the Wacker process can be used in industry for the kiloton scale production of oxidized alkenes. It has been shown previously that CNTs can be used to accelerate the Wacker process by transporting electrons between Pd$^0$ and the Cu$^{2+}$ used to mediate air oxidation to regenerate the Pd$^{2+}$ catalyst. See, for example, Schnorr, J. M.; Swager, T. M., *J. Mater. Chem.* 2011, 21, 4768-4770, which is incorporated by reference in its entirety. Reaction of Pd$^{2+}$ with ethylene results in Pd$^0$, which is a reducing agent that can quench the positive charge (p-type) carriers of SWCNTs, resulting in a chemiresistive response in the form of decrease in conductance.

The following Scheme 2 shows steps for the Hoechst-Wacker process.

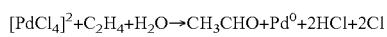

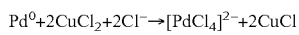

In the Wacker process (described in Scheme 2), the metal-alkyl product of the first reaction step further undergoes β-hydride elimination, which, after reoxidation, can result in the regeneration of the original palladium(II) species used to catalyze the reaction and release of the oxidized alkene. As the Pd$^{2+}$ is capable of the same chemistry as the Co(III) porphyrins as described in Scheme 1, but with a mechanism for recovery, a Pd$^{2-}$ compound or other related compounds that can perform this reactivity can give rise to a reversible ethylene sensor in a CNT, conducting polymer, metal oxide, or semiconductor composite. In the case that there is no recovery mechanism and the Pd$^0$ persists after reaction with the alkene, the system can function as a dosimeter. However, as the organocobalt(III) porphyrins formed through the mechanism depicted in Scheme 1 cannot undergo β-hydride elimination due to lack of an open coordination site cis to the alkyl group as a result of the porphyrinato ligand scaffold, the Wacker-type recovery mechanism is unavailable. Resetting the Co(III) porphyrin-CNT sensor after the Co(III) complex reacts with ethylene can be accomplished by the protonolysis of the resulting Co—C bond to give the free Co(III) complex again or by homolytic cleavage of the Co—C bond to give the Co(II). radical followed by oxidation of the Co(II). back to Co(III). The Co(III) porphyrin can be simply adsorbed to the conductive material, or attached through coordination to the Co(III) or through a covalent linkage to the porphyrin.

Other conductive materials other than carbon nanotubes can also be used. Conducting polymers (CPs), C$_{60}$, inorganic semiconductors, and metal oxides could also give a chemiresistive response to ethylene in a composite with these transition metal complexes. Furthermore, in an alkene sensing scheme based on a Wacker mechanism, the conducting material (CNTs, CPs, or metal oxides) can serve either in the electron-transfer mediator role that is occupied by CuCl$_2$ in the traditional Wacker mechanism (Scheme 2) or possibly in the direct electron acceptor role occupied by molecular oxygen. See, for example, Piera, J.; Bäckvall, J-E., *Angew. Chem. Int. Ed.* 2008, 47, 3506-3523, which is incorporated by reference in its entirety. The polyoxometalate (POM) phosphomolybdovanadate [H$_{(3+x-y)}$PMo$_{(12-x)}$V$_x$O$_{40}$]$^{y-}$ can function as an electron-transfer mediator between Pd and O$_2$ in a Wacker-like catalytic process, suggesting that metal oxides can also provide this function. Concomitant with the reduction of the semiconductor in order to reoxidize the metal complex can be a significant change in conductance of the semiconductor. The reduced metal complex can decrease the conductance of a p-type semiconductive material and increase the conductance of a n-type semiconductive material. See, for example, Grate, J. H.; Hamm, D. R.; Mahajan S. Palladium and Phosphomolybdovanadate Catalyzed Olefin Oxidation to Carbonyls; In *Polyoxometalates: From Platonic Solids to Antiretroviral Activity*; Pope, M. T; Müller A., Eds.; Kluwer: Dordrecht, 1994; p 281-305, which is incorporated by reference in its entirety.

The reactivity of the Pd(II) complexes in the Wacker reactions can be modulated by the addition of different ligand systems. The ligands can include bipyridyl types of ligands and quinones. These ligands serve to keep the metals in an active monomeric state and prevent the formation of colloidal metal particles. These ligands can be attached to the conducting material through a covalent linkage. The activation of alkenes toward reaction by nucleophiles can be caused by metal ions potentially including Mn, Re, Fe, Ru, Os, Co, Rh, Ir, Ni, Pd, Pd, Cu, Ag, Au, or Hg, or combinations thereof. Specific metal oxidation state and ligands can be necessary to create the needed reactivity.

A preferred analyte is ethylene, but this sensory scheme can be made to work with many volatile alkenes or alkynes. Sensors can be created for the detection of, acetylene, 1-methylcyclopropene, styrene, isoprene, butadiene, propene, and 1-hexene. To create selective responses for specific analytes, the nature of the metal and its ligands can be selectively chosen. For example a strained ring system like 1-methylcyclopropene can have higher reactivity than other alkenes, and selective detection schemes can be developed. Selectivity for ethylene can be afforded by creating highly restricted environments around the metal centers that are too large for other analytes to bind.

EXAMPLES

General Methods and Instrumentation (6,5) chirality-enriched SWNTs (SG65) were purchased from SouthWest NanoTechnologies. Ethylene gas (99.5% and 1.001% diluted by nitrogen), carbon monoxide gas, and acetylene gas (99.5%) were purchased from Airgas. 5,10,15,20-Tetrakis(pentafluorophenyl) porphyrin (tpfppH$_2$) was purchased from Frontier Scientific. Perchloric acid (70%) was purchased from Sigma-Aldrich. Aluminum oxide (activated, neutral, Brockmann Grade I, 58 Å) was purchased from Alfa Aesar. Solvents were purchased from Sigma-Aldrich or Avantor Performance Materials (Macron Fine Chemicals or J. T. Baker) and used as received.

UV-Vis spectra were recorded on a Cary 4000 UV-visible spectrophotometer. FT-IR spectroscopy was performed with use of a Thermo Scientific Nicolet 6700 FT-IR spectrometer (ATR mode, Ge). NMR spectra were recorded using a Bruker Avance 400 MHz NMR spectrometer. Profilometry measurements were taken using a Veeco Dektak 6M Stylus Profiler fitted with a 2.5 μm radius tip.

Synthetic Procedures 5,10,15,20-Tetraphenylporphyrin (tppH$_2$), 5,10,15,20-tetraphenylporphyrinatocobalt(II) [Co(tpp)], 5,10,15,20-tetrakis(pentafluorophenyl)porphyrinatocobalt(II) [Co(tpfpp)], chloro(5,10,15,20-tetraphenylporphyrinato)cobalt(III) [Co(tpp)Cl], and 5,10,15,20-tetraphenylporphyrinatocobalt(III) perchlorate dihydrate [Co(tpp)(H$_2$O)$_2$]Cl$_4$ were synthesized according to literature procedures. See, for example, Adler, A. D.; Longo, F. R.; Finarelli, J. D.; Goldmacher, J.; Assour, J.; Korsakoff, L., *J. Org. Chem.* 1966, 32, 476; Dorough, G. D.; Miller, J. R.; Huennekens, F. M., *J. Am. Chem. Soc.* 1951, 73, 4315-4320; Kadish, K. M.; Araullo-McAdams, C.; Han, B. C.; Franzen, M. M., *J. Am. Chem. Soc.* 1990, 112, 8364-8368; Sakurai, T.; Yamamoto, K.; Naito, H.; Nakamoto, N., *Bull. Chem. Soc. Jpn* 1976, 49, 3042-3046; Sugimoto, H.; Ueda, N.; Mori, M., *Bull. Chem. Soc. Jpn* 1981, 54, 3425-3432, each of which is incorporated by reference in its entirety.

Synthesis of 5,10,15,20-tetrakis(pentafluorophenyl)porphyrinatocobalt(III) perchlorate dihydrate [Co(tpfpp)(H$_2$O)$_2$]ClO$_4$. [Co(tpfpp)] (0.060 g, 0.058 mmol) was dissolved in methanol (60 mL). A 10% aqueous HClO$_4$ solution (2 mL) was added, and air was bubbled through the solution while stirring for 72 h at rt. The reaction mixture was concentrated with use of rotary evaporation. The resulting purple crystals were isolated by vacuum filtration and allowed to dry under air to give the product (0.043 g) in 66% yield.

Synthesis of chloro(5,10,15,20-tetrakis(pentafluorophenyl)porphyrinato)cobalt(III) [Co(tpfpp)Cl]. [Co(tpfpp)] (0.060 g, 0.058 mmol) was dissolved in methanol (60 mL). Concentrated HCl (0.6 mL) was added, and air was bubbled through the solution while stirring for 72 h at rt. The reaction mixture was concentrated with use of rotary evaporation. The resulting purple crystals were isolated by vacuum filtration and allowed to dry under air to give the product (0.023 g) in 37% yield.

Figure 3:
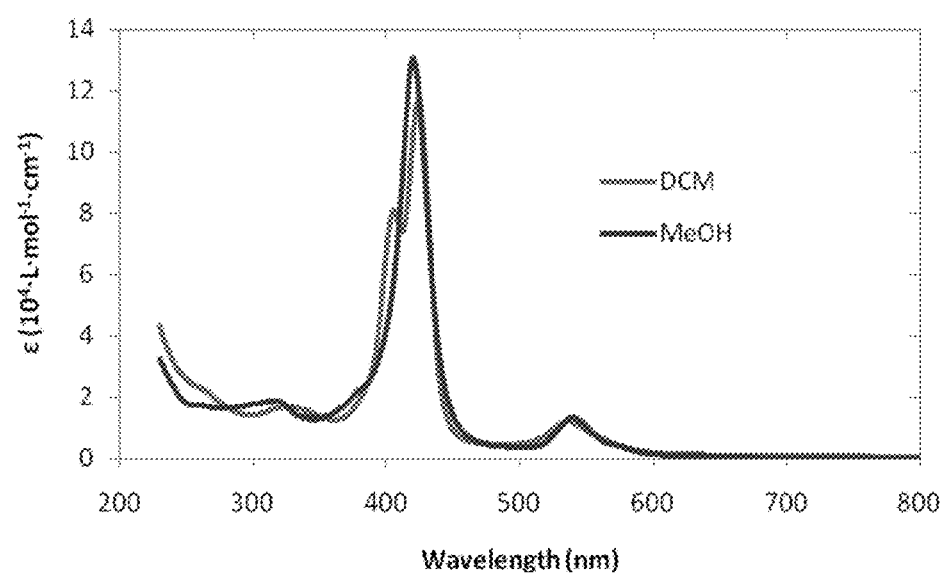
FIG. 3 shows UV-Vis spectrum of $[Co(tpfpp)]ClO_4$ in dichloromethane (DCM) and in methanol (MeOH).
Figure 4:
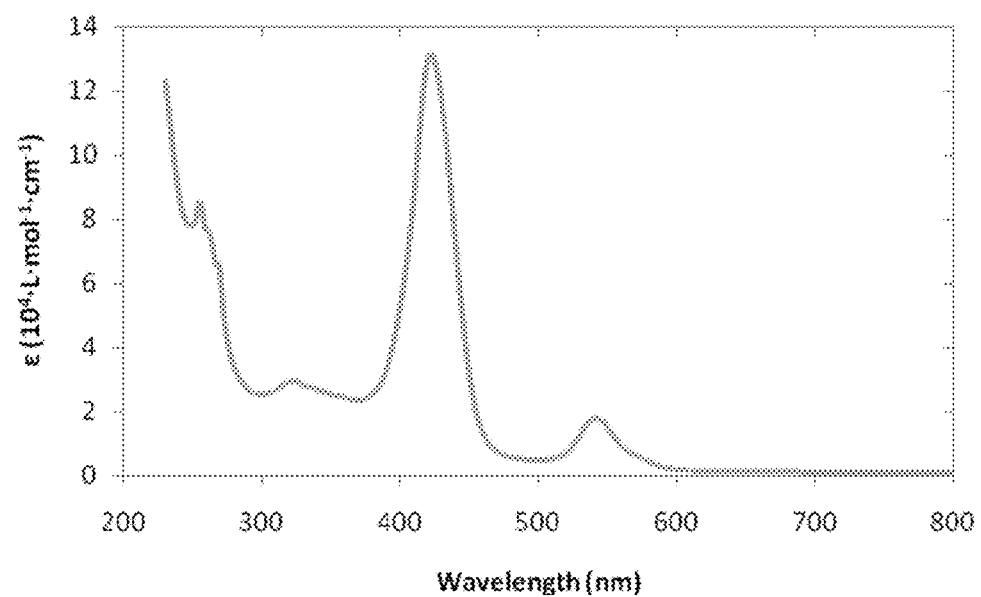
FIG. 4 shows UV-Vis spectrum of [Co(tpfpp)Cl] in dichloromethane.
Figure 5:
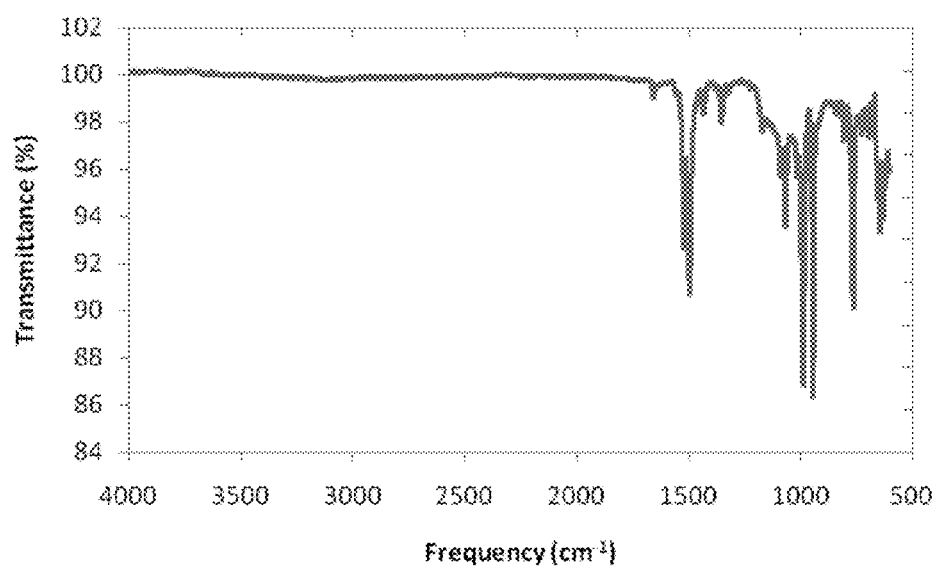
FIG. 5 shows IR spectrum of $[Co(tpfpp)(H_2O)_2]ClO_4$.
Figure 6:
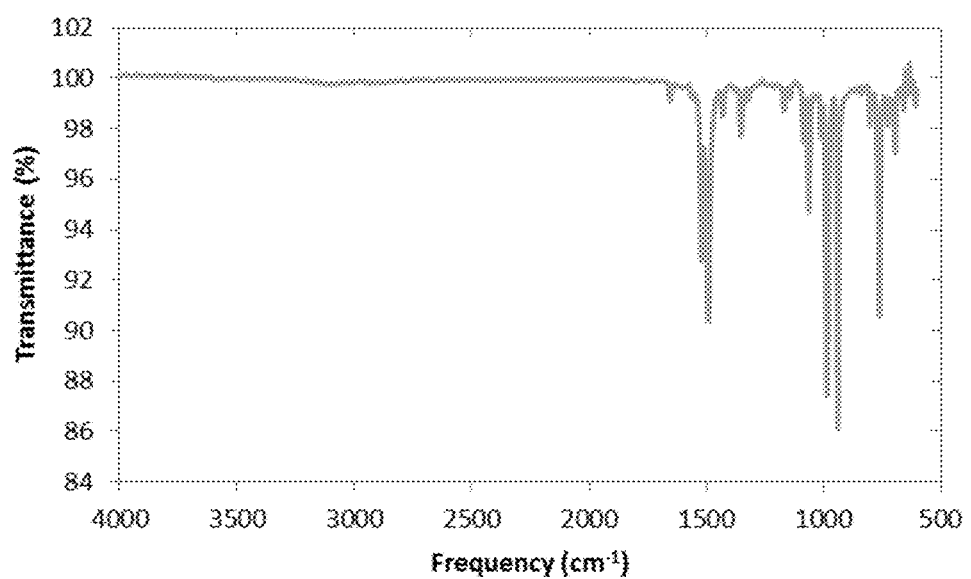
FIG. 6 shows IR spectrum of $[Co(tpfpp)(H_2O)_2Cl]$.

FIG. 3 shows UV-Vis spectrum of [Co(tpfpp)]ClO$_4$ in dichloromethane (DCM) and in methanol (MeOH). FIG. 4 shows UV-Vis spectrum of [Co(tpfpp)Cl] in dichloromethane. FIG. 5 shows IR spectrum of [Co(tpfpp)(H$_2$O)$_2$]ClO$_4$. FIG. 6 shows IR spectrum of [Co(tpfpp)(H$_2$O)$_2$Cl].

Device Preparation

Devices were prepared on microscope glass slides (VWR) cleaned by sonication in acetone. The glass slides were fitted with a custom aluminum mask, and using a thermal evaporator purchased from Angstrom Engineering, a 10 nm layer of chromium (99.99%, R. D. Mathis) was deposited onto the glass, followed by 100 nm of gold (99.99%, R. D. Mathis).

In a typical device, 0.25 mg (21 μmol C) of SWNTs and 0.44 mmol porphyrin were suspended in 1.0 mL 1,2-dichlorobenzene and sonicated briefly at room temperature. The resulting dispersion was drop-casted using a micropipette onto the glass slide in between the gold electrodes. The solvent was removed in vacuo. The application of the dispersion followed by the removal of the solvent was repeated until the resistance across the SWNT network reached a resistance of 1-10 kΩ as measured by a multimeter.

Figure 7:
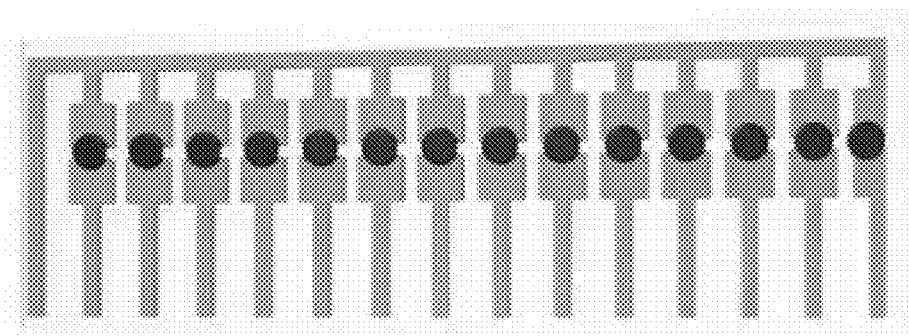
FIG. 7 shows schematic representation of a chemoresistive ethylene detector array.

FIG. 7 shows a schematic of a typical device, which is fabricated from a suspension of (6,5) chirality-enriched SWNTs and a given Co(III) porphyrin in 1,2-dichlorobenzene (DCB). Initial optimization experiments showed that sensitivity to ethylene was maximized at a mole ratio of 21:1 porphyrin:C$_{SWNT}$; this mole ratio was kept constant throughout our gas detection studies. This suspension is sonicated briefly and then drop-casted to form films of the composite material that are 0.3 μm thick in between gold electrodes (1 mm gap) in a 14 channel array with a shared counter-electrode, allowing for simultaneous measurements with different porphyrin-SWNT composites in multiplicate. The array setup can also be used to make devices with channels of different composites sensitive to ethylene gas for the purposes of redundancy and the ability to differentiate between responses to ethylene and to interferents.

Gas Detection Measurements

Gas detection measurements were acquired by connecting the gold electrodes of the device to a PalmSens EmStat potentiostat with a MUX16 multiplexer. For ethylene detection measurements, the device is enclosed in a PTFE chamber, and a gas mixer system is used to deliver to the chamber low concentrations of ethylene diluted by nitrogen. The gas mixer is comprised of two digital mass flow controllers purchased from Sierra Instruments. A MicroTrak Mass Flow Controller is used to deliver up to 4 mL/min of a mixture of 1% ethylene in nitrogen that is further diluted in the gas mixer by nitrogen delivered by the other MFC at 2.00 L/min. The potentiostat was used to apply a constant potential of 0.100 V across the electrodes, and the current was recorded using PSTrace software (v. 3.0) as the device was exposed to varying concentrations of ethylene for 100 s at a time with at least 50 s between successive measurements. Acetylene measurements were made in a similar manner, using acetylene in the place of the 1% ethylene in nitrogen. For measuring device response to volatile liquid organic compounds and to water, a KIN-TEK gas generator system was used after calibration for each compound. Data for ethylene detection measurements were corrected to a linear fit of the baseline current that was measured prior to gas exposures; for other analytes, the data were corrected to a linear fit of the baseline across the entire data acquisition time.

Figure 8:
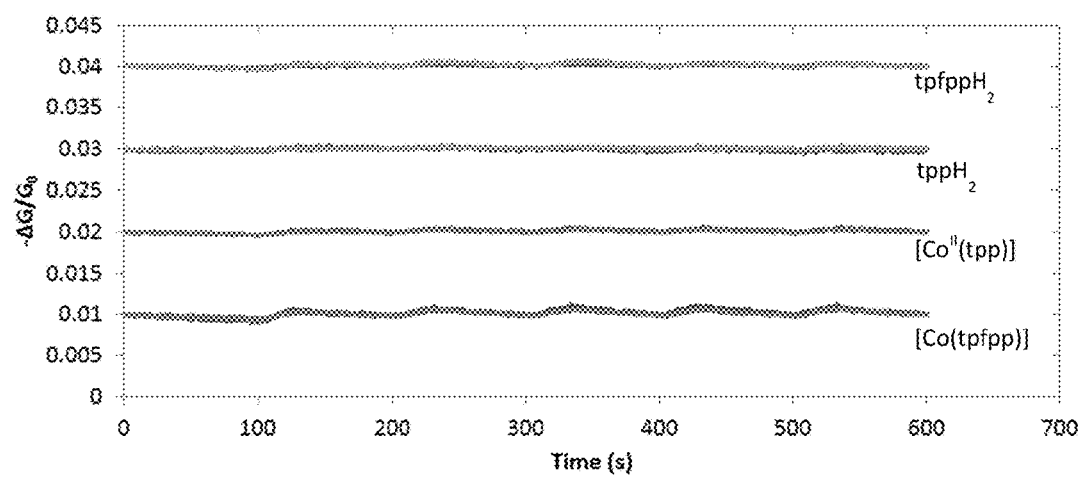
FIG. 8 shows chemoresistive responses of $tpfppH_2$, $tppH_2$, $[Co^{II}(tpp)]$, and $[Co^{II}(tpfpp)]$ in SWNT composites to 20 ppm ethylene diluted in nitrogen applied for 30 s at a time at 100, 200, 300, 400, and 500 s.

FIG. 8 shows chemoresistive responses of tpfppH$_2$, tppH$_2$, [Co$^{II}$(tpp)], and [Co$^{II}$(tpfpp)] in SWNT composites to 20 ppm ethylene diluted in nitrogen applied for 30 s at a time at 100, 200, 300, 400, and 500 s.

Ethylene Detection Measurement

For ethylene detection measurements, the device is enclosed in a PTFE chamber, and the gold electrodes are attached to a potentiostat equipped with a multiplexer. A gas mixer system is used to introduce low concentrations of ethylene into a stream of nitrogen as the carrier gas passing over the device at a fixed flow rate. The potentiostat applies a constant potential of 0.100 V across the electrodes and records the current as the device is exposed to varying concentrations of ethylene. The change in current that results from exposure to ethylene is converted to change in conductance ($-\Delta G/G_0$), which is taken as the device's response.

Figure 9A:
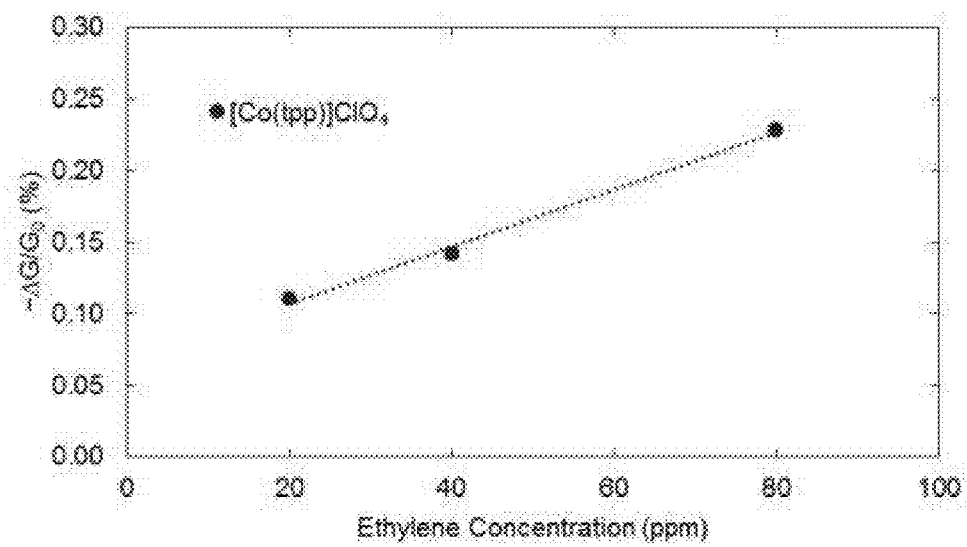
FIG. 9A shows linear chemoresistive responses of Co(III) porphyrin-SWNT devices to various concentrations of ethylene diluted in nitrogen.
Figure 9B:
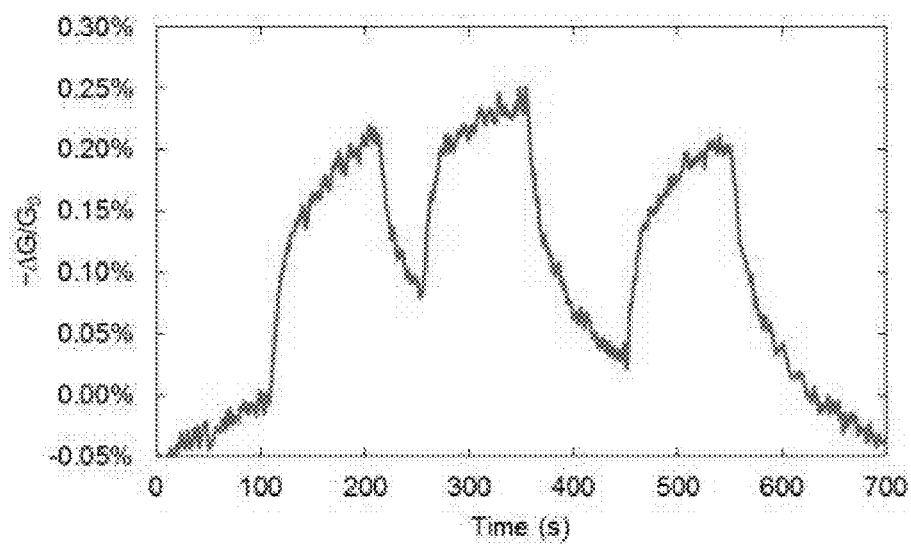
FIG. 9B shows response of a $[Co(tpp)]ClO_4$-based device 100 s exposures of 80 ppm ethylene diluted in nitrogen.

The responses that resulted from exposing the Co(III)-based devices to various low concentrations of ethylene for 100 s at a time are shown in the calibration curve in FIG. 9A. Measurements up to 80 ppm were performed and were able to detect ethylene concentrations down to below 20 ppm. The devices behaved reversibly (FIG. 9B) and responded linearly to ethylene in this range of concentrations, allowing for direct quantitation of ethylene with use of a calibration curve as shown in FIG. 9A. The use of a weakly coordinating anion is important to improving sensitivity to ethylene as well as the fluorination of the meso phenyl rings in the ligand. Therefore, analogous compounds with other non-coordinating anions (e.g., $BF_4^-$ and $CF_3SO_3^-$) or with other dianionic macrocyclic ligands such as phthalocyanines or other porphyrins, including those that are biologically derived, can be used. As noted previously, pristine SWNTs do not give an appreciable chemoresistive response to ethylene at 20 ppm.

Stability and Selectivity of Metal Macroycycle-Carbon Based Sensor

As the Co(III) center in these porphyrin complexes are already at the higher of the two most common oxidation states for cobalt and are in fact synthesized from their Co(II) precursors through aerobic oxidation, we expected the devices fabricated from them to be stable to oxidation by molecular oxygen in ambient conditions.

Figure 10:
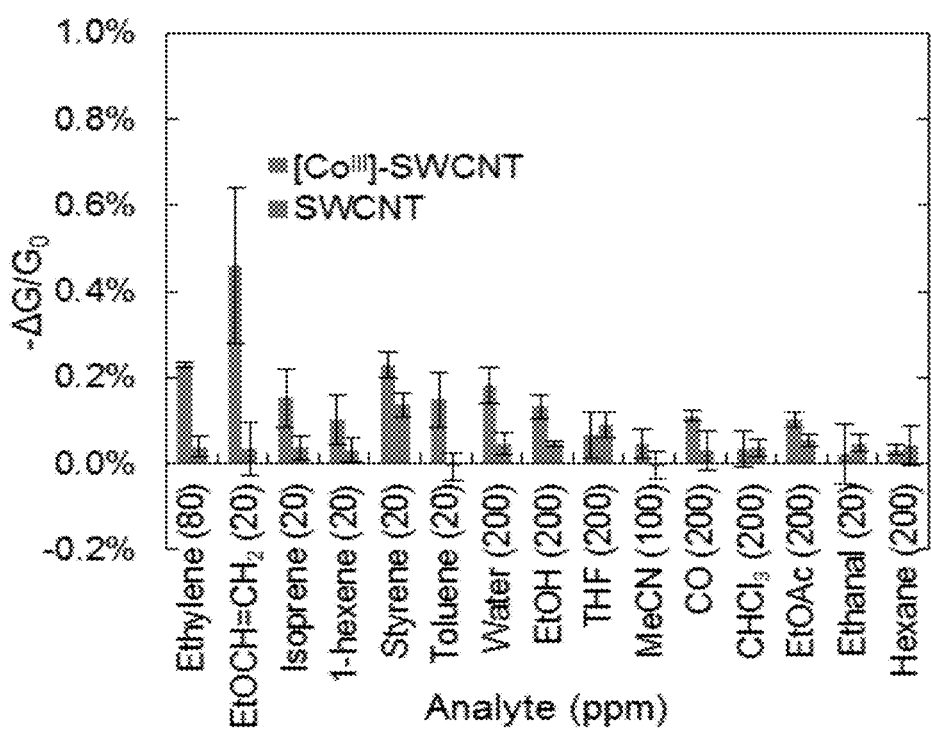
FIG. 10 shows responses of $[Co(tpp)]ClO_4$— SWNT devices to various chemical interferents diluted by nitrogen in comparison to their responses to 80 ppm ethylene in nitrogen.

To assess the selectivity of the devices toward ethylene, we measured the responses of [Co(tpp)]ClO$_4^-$-SWNT devices to water and to several volatile organic compounds chosen to represent a wide range of organic functional groups. The results are shown relative to the response to 80 ppm ethylene in FIG. 10.

Palladium Based Gas Sensor

Figure 11:
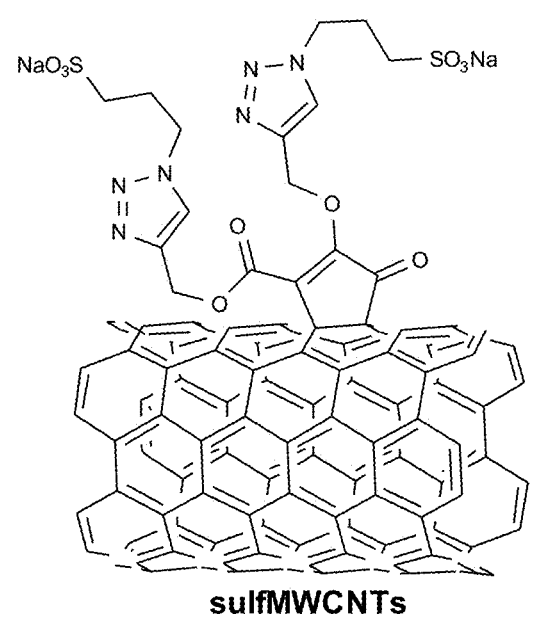
FIG. 11 shows structure of sulfonated MWCNTs.

The following example describes the fabrication and use of sensors using sulfonated MWCNTs and Pd(OCOCF$_3$)$_2$ as the sensing layer. Sulfonated MWCNTs (sulfMWCNTs) were synthesized. See, for example, J. M. Schnorr, T. M. Swager, J. Mater. Chem., 2011, 21, 4768-4770; PCT/US2009/006512, each of which is incorporated by reference in its entirety. FIG. 11 shows the structure of sulfonated MWCNTs.

Two samples of sulfMWCNTs were prepared and the density of sulfonate groups was determined to be 1 per 30 MWCNT carbon atoms (highsulfMWCNTs) and 1 per 120 MWCNT carbon atoms (lowsulfMWCNTs), respectively. Additionally, pristine MWCNTs (obtained from Bayer Group, Baytubes® C 150 P, >95% purity) were used.

The sensor substrate is a gold electrode pattern on a glass slide. The electrode gap size is 1 mm. Glass slides (VWR Microscope Slides) were cleaned by ultrasonication in acetone for 3 min, followed by ultrasonication in water for 3 minutes. Subsequently, the slides were dried under nitrogen and then scored with a glass cutter to yield 6 segments (0.5 inch×1 inch each). The gold layer was deposited using a shadow masks in a gold sputter coater (Polaron SC7620) at 18 mA for 2 times 180 sec. yielding a layer thickness of ca. 45 nm. The glass slide was then broken into 6 pieces carrying one pair of electrodes at a distance of 1 mm each.

MWCNT/selector suspensions were prepared by mixing a suspension of MWCNTs (highsulfMWCNTs, lowsulfMWCNTs, or pristine MWCNTs) in water at a concentration of 1 mg/mL with a solution of Pd(OCOCF$_3$)$_2$ (3.3 mg/mL in water) at a ratio of 1:1. The MWCNT layer was then prepared by drop-casting 2 times 5 µL of the MWCNT/Pd(OCOCF$_3$)$_2$ suspension between the electrodes of the substrate followed by drying in air.

Figure 12:
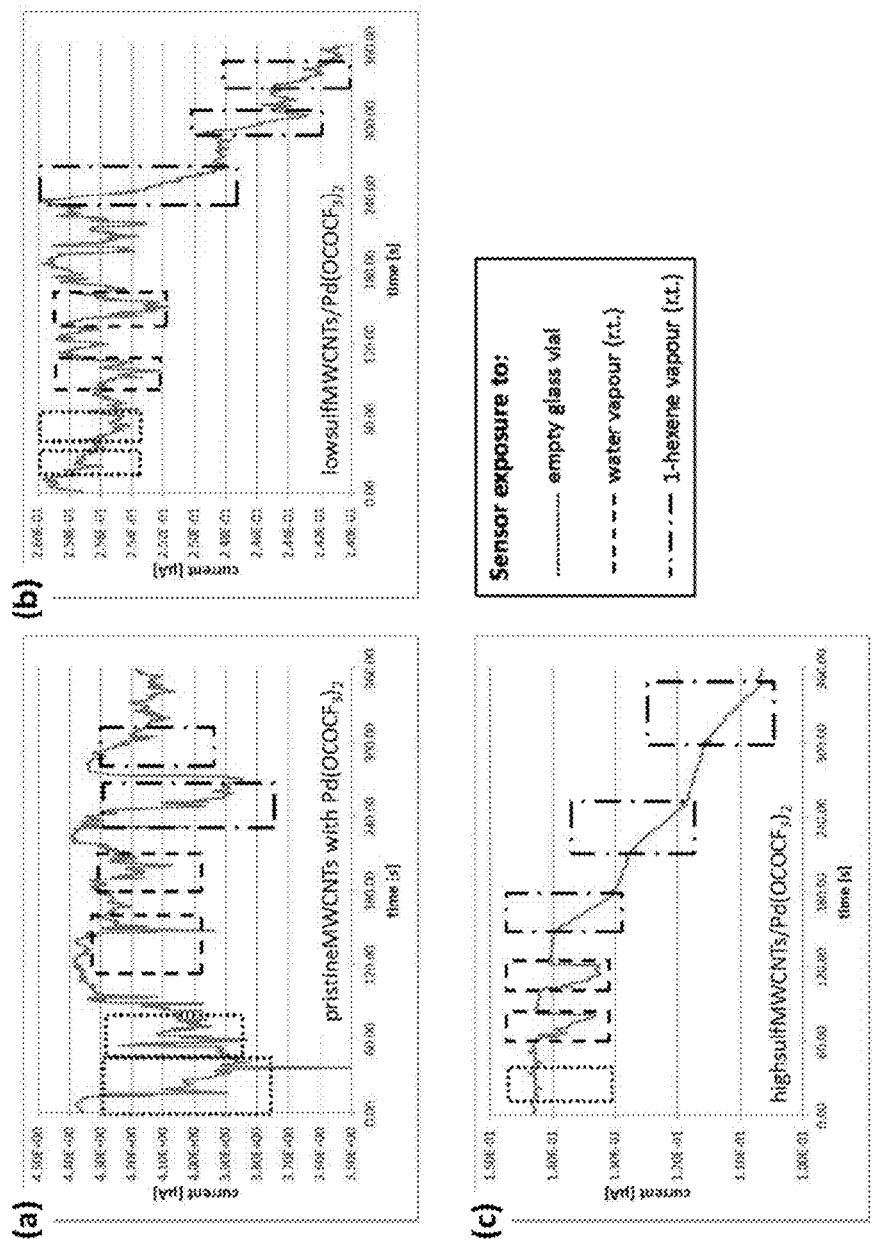
FIG. 12 shows the sensing response of $Pd(OCOCF_3)_2$ with pristine MWCNTs (a), low sulfonate density (1/120) MWCNTs (b), and high sulfonate density MWCNTs (c) to an empty vial (control) as well as water and 1-hexene.

Sensing properties of the devices were measured by monitoring the conductivity change of sensors upon exposure to analyte. The sensors deposited on the electrodes were connected to a potentiostat (Autolab PGSTAT 20, Eco Chemie) and the current was monitored at a constant potential of 0.05 V. The sensor was then exposed to the analyte by holding it directly over a 20 mL glass vial containing ca. 2 mL of either water or 1-hexene with cotton wool. A control experiment with an empty glass vial was performed as well. Sensing experiments were performed in ambient atmosphere at room temperature. Sensing traces of sensors based on Pd(OCOCF$_3$)$_2$ with pristine MWCNTs, low sulfonate density (1/120) MWCNTs, and high sulfonate density (1/30) MWCNTs, respectively, upon exposure to an empty glass vial, water, and 1-hexene are shown in FIG. 12.

Other embodiments are within the scope of the following claims:

What is claimed is:

1. A method of sensing an analyte, comprising:
   exposing a sensor to a sample, the sensor including:
   a conductive region in electrical communication with at least two electrodes, the conductive region including a conductive material and an alkene-interacting metal complex, the alkene-interacting metal complex including a metal macrocycle complex capable of forming a stable complex with a sterically protected metal center;
   producing a chemiresistive response and regenerating the metal complex that reacts with an additional alkene; and
   measuring an electrical property at the electrodes.

2. The method of claim 1, wherein the sample is a gas.

3. The method of claim 1, wherein the electrical property is resistance or conductance.

4. The method of claim 1, wherein the analyte is ethylene, 1-methylcyclopropene, butadiene, isoprene, carbon monoxide, or acetylene.

5. The method of claim 1, wherein the conductive material includes a carbon nanotube, graphite, graphene, an alkene-interacting metal complex, a conductive polymer, a metal oxide, or an inorganic semiconductor.

6. The method of claim 1, wherein the alkene-interacting metal complex includes a metal macrocycle complex capable of forming a stable complex by reaction with an alkene, wherein a chemiresponsive composition comprising a metal complex including a metal binds to and activates an alkene such that it reacts with a nucleophile to provide a metal complex with a metal carbon single bond.

7. The method of claim 1, wherein the metal macrocycle complex includes a phthalocyanine or a porphyrin, such as 5,10,15,20-tetraphenylporphyrinato cobalt or 5,10,15,20-tetrakis(pentafluorophenyl)porphyrinato cobalt.

8. The method of claim 1, wherein the metal of the macrocycle complex includes Mn, Re, Fe, Ru, Os, Co, Rh, Ir, Ni, Pd, Pd, Cu, Ag, Au, or Hg.

9. The method of claim 1, wherein the metal macrocycle complex includes a non-coordinating anion.

10. The method of claim 9, wherein the anion includes $Cl^-$.

11. The method of claim 9, wherein the anion includes $ClO_4^-$.

12. The method of claim 1, wherein the alkene-interacting metal complex includes a palladium ion.

13. The method of claim 12, wherein the alkene-interacting metal complex includes a palladium (II) trifluoroacetate or palladium (II) acetate.

* * * * *